United States Patent [19]

Makler

[11] Patent Number: 4,946,849

[45] Date of Patent: Aug. 7, 1990

[54] METHOD FOR THE TREATMENT OF MALARIA

[75] Inventor: Michael T. Makler, Portland, Oreg.

[73] Assignee: Flow Incorporated, Portland, Oreg.

[21] Appl. No.: 418,086

[22] Filed: Oct. 10, 1989

[51] Int. Cl.$^5$ .............................................. A61K 31/47
[52] U.S. Cl. ..................................................... 514/313
[58] Field of Search ......................................... 514/313

[56] References Cited

PUBLICATIONS

Chemical Abstracts 107:223327r (1987).
Merck Index, 9th Ed., 1976 (compounds 2873-2874—p. 381).
Chemical Abstracts 109:167179w (1988).
Bleday, R. et al., Arch. Surg., 121:1272-1275 (1986).
Weiss, M. J. et al., Proc. Nat. Acad. Sci., 84:5444-5448 (1987).
Bodden et al., Biophy. Res. Comm., 135:574-582 (1986).
Scheibel, L., Proc. Nat. Acad. Sci., 84:7310-7314.
Bullough, D. A. et al., J. Biol. Chem., 264:9155-9163 (1989).
Choi, I. and Mugo, J. L., Mol. Biochem. Parasit., 31:71-78 (1988).
Rotenberg, S. A. et al., Proc.Annu. Meet. Am. Assoc. Cancer Res., 30:a25 (1989).
Trager, W. and Jensen, J., Science, 193:673-675 (1976).
Makler, M. T. et al., Cytometry, 8:568-570 (1987).
Wernsdorfer, W. H. et al., chapter 51, "Recent Progress of Malaria Research", Malaria, Principles and Practices of Malariology, vol. 2, Churchill Livingston Co., London (1988).
Bodden, W. L. et al., "Demonstration of Calmodulin (CAM Inhibition by Cytotoxic Antimitochondrial Agents (Meeting Abstract)", Proc. Annu. Meet. Am. Assoc. Cancer Res., 27:280 (1986).

Primary Examiner—Jerome D. Goldberg
Attorney, Agent, or Firm—Jay K. Malkin

[57] ABSTRACT

A safe and effective therapeutic method for treating malaria. To accomplish treatment, anti-parasite agents are administered which consist of dequalinium salts. The salts are highly effective against chloroquine resistant/sensitive strains of human P. falciparum at low concentration levels.

5 Claims, No Drawings

METHOD FOR THE TREATMENT OF MALARIA

BACKGROUND OF THE INVENTION

The present invention generally relates to a disease treatment method, and more specifically to a method for treating malaria.

Malaria is a dangerous disease caused by a protozoic parasite which invades a host's liver cells and erythrocytes. It is one of the most wide-spread infectious diseases. The World Health Organization estimates that 200,000,000 people are infected with the malaria parasite annually. These people mainly reside in the tropics. One million cases of malaria were reported in the U.S. in 1940. At that time, effective measures were introduced which virtually eliminated the disease, which is transmitted by the female Anopheles mosquito. However, the Anopheles mosquito is still present in many of the Southern and Western parts of the U.S. During the early 1970's, there were several cases of malaria reported in Louisiana and California. These were attributed to returning veterans from the Viet Nam War who harbored the parasite.

As tropical regions of the world become more accessible through improved modes of transportation, travel into these areas is increasing. This has resulted in significantly more cases of malaria being reported in travelers returning from these areas. One percent (1%) of all people infected with the malaria parasite die from the disease (2,000,000 people per year). There are four species of Plasmodium which infect humans and cause malaria. These include *P. falciparum*, *P. vivax*, *P. ovale*, and *P. malariae*. *P. falciparum* is the most serious species. It is responsible for cerebral malaria which is associated with a 50% mortality rate.

The life cycle of a Plasmodium parasite involves the interrelationship between an Anopheles mosquito vector and a mammalian host. When an uninfected female Anopheles mosquito bites and ingests blood from a host harboring the sexual forms of the Plasmodium parasite, the parasitic life cycle begins. In the Anopheles, the male and female gametocytes fuse and travel after several stages of development to the salivary glands of the mosquito. The parasite at this stage is called a "sporozoite." If the infected mosquito bites a new host, the sporozoites are injected into the host's blood. Thereafter, they travel to the liver within 30 minutes, where they enter a liver cell. In the liver cell, one sporozoite multiplies and forms about 10,000–20,000 merozoites. These merozoites are released from the liver cells in 10–12 days. Each of the released merozoites immediately invades an erythrocyte. In 48 hours, each merozoite forms another 10–12 merozoites which are in turn released from the erythrocyte only to invade another 10–12 erythrocytes.

The clinical manifestations of the disease include fever, headaches, sweating, vomiting, and prostration. These manifestations occur simultaneously with merozoite release from the erythrocytes. The erythrocyte reinvasion occurs until the host dies, or until the host's immune system is able to control and suppress merozoite activity. At some point, the merozoites (previously asexual) differentiate into male and female gametocytes. The technical and scientific basis for this transformation is an active area of current medical research. If a female Anopheles then bites a new host at the time of gametocyte formation, the life cycle of the parasite is completed.

The most susceptible human hosts for the disease are infants and pregnant women having suppressed immunity. Recently, deaths have been reported in adult male AIDS patients caused by cerebral malaria. In addition, non-immune travelers into high-risk malaria areas are also susceptible to the disease, especially with respect to chloroquine and quinine resistant malaria.

There is a natural immunity to malaria which develops in persons living in high-risk malaria areas. This immunity appears to depend upon the continual presence of low parasite levels in the host's body. This conclusion is drawn from many studies which demonstrate that when persons living in high-risk malaria areas leave for a variety of reasons and travel to low risk areas, they substantially lose their immunity.

Many chemical agents have been developed to treat malaria. For example, chloroquine and quinine have been used over the past thirty years. However, chloroquine-resistant malaria strains of *P. falciparum* (the malaria parasite responsible for 1.6 million deaths annually) have spread from two to seventy countries throughout the world. In addition, there are twelve countries which have reported quinine-resistant strains of *P. falciparum*. As a result, many corporations and governments have spent billions of dollars in attempts to develop new drug therapies for the disease, with an inconsequential degree of success.

The present invention represents a new and effective therapeutic method for treating malaria. It offers a superior degree of efficacy, safety, and utility compared with currentlyused compounds.

SUMMARY OF THE INVENTION

It is an object of the present invention to provide a method for treating malaria having an improved degree of effectiveness.

It is another object of the invention to provide a method for treating malaria using a chemical compound characterized by a low degree of human toxicity.

It is a further object of the invention to provide a method for treating malaria which uses readily available, inexpensive materials.

It is a still further object of the invention to provide a method for treating malaria which uses a chemical compound that is effective at low concentration levels.

It is an even further object of the invention to provide a method for treating malaria which is highly effective against parasites having resistance to currently available antiparasitic agents, including chloroquine and quinine.

In accordance with the foregoing objects, the present invention involves a safe and effective method for malarial infections which involves the systemic administration of a selected salt of dequalinium. Dequalinium salts have a high degree of effectiveness against chloroquine resistant/sensitive strains of human *P. falciparum* at minimal (nanogram) quantities. Accordingly, the dequalinium compounds described herein represent an advance in the art of malaria control.

These and other objects, features, and advantages of the invention shall be described below in the following detailed description of a preferred embodiment, experimental examples, and drawing figures.

BRIEF DESCRIPTION OF THE DRAWINGS

FIG. 1 is a graphical representation of test data obtained when chloroquine-resistant strains of *P. falcipa-*

*rum* were treated with a dequalinium salt at nanogram quantities.

DETAILED DESCRIPTION OF A PREFERRED EMBODIMENT

The present invention involves a highly effective therapeutic method for treating malaria described in detail herein. In accordance with the invention, malaria is controlled by the administration of a selected dequalinium salt. Dequalinium and its salts were originally synthesized and patented in Britain. Specifically, these materials are described in British Patent No. 745,956 issued in 1956. They are also discussed in the Merck Index, 9th ed., 1976 (compounds 2873-2874 on page 381).

Dequalinium and its salts (chloride, salicylate, bromide, iodide, and acetate) have been used extensively as topical anti-bacterial and anti-fungal compounds in skin medications, ophthalmic ointments, vaginal creams, and mouthwashes. They have also been used as anti-neoplastic agents, and in oral solutions for oral/buccal diseases. For example, Romanian Patent No. 76918 discloses the topical use of dequalinium compounds to control *Sarcoptes scabiei* (a mite). In addition, dequalinium was approved for topical use as a wound dressing by the FDA in 1976.

Specific studies have been conducted in order to evaluate the anti-neoplastic characteristics of dequalinium materials. As discussed in Bleday, R. et al., "Inhibition of Rat Colon Tumor Isograft Growth With Dequalinium Chloride" Arch. Surg. 121:1272-1275 (1986) and Weiss, M. J., et al., "Dequalinium, A Tropical Antimicrobial Agent, Displays Anticarcinoma Activity Based On Selective Mitochondrial Accumulation" *Proc. Nat. Acad. Sci.*, 84:5444-5448 (1987), tumor-bearing animal (rat) studies were conducted involving dequalinium chloride. The rats receiving a sublethal dose (1.0 mg/kg) by subcutaneous, intraperitoneal, or implant-osmotic pump administration all survived and demonstrated significant tumor growth inhibition.

Most dequalinium compositions for topical use including mouthwashes have a dequalinium concentration of 0.001% (10 micrograms/ml). This concentration level is many thousand times greater than the dequalinium concentration levels which are capable of inhibiting *P. falciparum* growth, as described herein below.

Dequalinium materials are chemically characterized as lipophilic cationic compounds. The basic structure of a dequalinium salt is as follows:

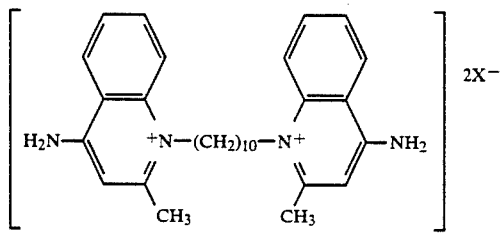

[X = Cl, Br, I, acetate, or salicylate]

This material is known as 1,1'-(1,10-Decanediyl)bis-[4-amino-2-methylquinolinium] salt or as a 1,1'-decamethylenebis[4aminoquinaldinium] salt. The chloride salt consists of $C_{30}H_{40}Cl_2N_4$ (C=68.30%; H=7.64%; Cl=13.44%; and N=10.62%) with a molecular weight of 527.60. It has an $LD_{50}$ s.c. in mice of 70 mg/kg. In addition, sterilization of *in vitro* cultures of *P. falciparum* occurs at concentration levels of 1.0 microgram/ml or less, as described in greater detail below.

The acetate salt consists of $C_{34}H_{46}N_4O_4$ (C=71.05%; H=8.07%; N=9.75%; and O=11.14%) with a molecular weight of 574.74.

In accordance with the invention, it has been discovered that dequalinium compounds are highly effective against malaria parasites in humans and other warm-blooded animals. To control malaria parasites in an animal subject, a selected dequalinium salt (e.g. dequalinium chloride) is administered in an aqueous solution (e.g. water) either orally, intravenously, intraperitoneally or subcutaneously at a preferred dequalinium salt concentration level of about 1.0 microgram/ml or less. In a preferred embodiment, the total dosage of compound administered would be about 7 mg of dequalinium salt per kg of body weight over a 3-5 day period. However, the total compound dosage may be experimentally varied depending upon a variety of factors, including the age, size (weight), and nutritional status of the subject, as well as the exact concentration level of the compound and extent of parasitic infection.

There are numerous theoretical mechanisms of action which may explain the effectiveness of dequalinium compounds in controlling malaria. One mechanism involves the possible accumulation of dequalinium compounds in mitochondria. This mechanism is discussed in Weiss, et al., *Proc. Nat. Acad. Sci.*, 84:5444-5448 (1987) with respect to the use of dequalinium as a topical therapeutic agent for neoplastic tissues. More specifically, dequalinium compounds may bind to calmodulin in parasite mitochondria. Calmodulin is an essential protein for the activation of phosphodiesterase which is necessary for cell growth as discussed in Bodden et al., "Selective Antimitochondrial Agents Inhibit Calmodulin" *Bioohv. Res. Comm.*, 35:574-582 (1986). It has also been shown in Scheibel, L. "Calcium and Calmodulin Antagonists Inhibit Human Malaria Parasites (Plasmodium Falciparum): Implications For Drug Design" *Proc. Nat. Acad. Sci.*, 84:7310-7314 (1987) that calmodulin antagonists generally inhibit human malaria parasites.

A second suggested mechanism of action involves the ability of dequalinium compounds to inhibit the ATPases of cellular tissues, as discussed in Bullough, D. A. et al., "Localization of Sites Modified During Inactivation of the Bovine Heart Mitochondrial $F_1$-ATPase By Quinacrine Mustard Using [$^3$H]Aniline as a Probe" *J. Biol. Chem.* 264:9155-9163 (1989). ATPases are present on the membranes of the parasitophorous vacuoles of *P. falciparum* parasites, and these enzymes are inhibited by proton pump inhibitors as discussed in Choy, I. and Mego, J. L., "Purification of Plasmodium Falciparum Digestive Vacuoles and Partial Characterization of the Vacuolar Membrane ATPase" *Mol. Biochem. Parasit.* 31:71-78 (1988).

Finally, an additional mechanism of action may involve the ability of dequalinium compounds to inhibit protein kinase C as discussed in Rotenberg, S. A. et al., "Inhibition of protein kinase C by the anticarcinoma agent dequalinium. Structure-activity relationships." *Proc. Annu. Meet. Am. Assoc. Cancer Res.*, 30:a25 (1989). However, there is no currently available information as to the role protein kinase C plays in the growth/development of malaria parasites.

Regardless of its suggested mechanism of action, dequalinium compounds are surprisingly effective in controlling the propagation of malaria parasites. This characteristic has not been suggested or recognized in the relevant chemical literature, which is primarily directed to the use of dequalinium compounds as topical anti-bacterial, anti-viral or antineoplastic agents.

EXPERIMENTAL TESTS

Numerous experiments were conducted regarding dequalinium compounds and their ability to control the growth of chloroquine-resistant and sensitive strains of *P. falciparum* malaria parasites. Specifically, two commonly-known strains of *P. falciparum* were obtained from the American Type Culture Collection (ATCC), namely, ATCC 50005 (chloroquine resistant) and ATCC 50028 (chloroquine sensitive). The methods of culture and culture materials used in the experiments described herein are known in the art and discussed in Trager W. and Jensen, J., "Human Malaria Parasites in Continuous Culture" *Science*, 93:673-675 (1976).

Assays for growth inhibition of *P. falciparium* were performed using the above parasites in standard 96-well test plates. All assays were performed in duplicate. The tests involved the use of a dequalinium chloride salt solution (from the Sigma Company of St. Louis, Mo.—product no. D3768) at concentration levels of 32, 16, 8, 4, 2, 1, and 0 nanograms/ml.

The parasites were permitted to incubate in the test media for 72 hours. At 24 hour intervals, new media and test substances were added, and an aliquot of the incubation mixture was removed for microscopic examination, In addition, the parasites were examined by flow cytometry using the techniques discussed in Makler, M. T., et al., "Thiazone Orange: A New Dye for Plasmodium Species Analysis" *Cytometry*, 8:568-570 (1987).

The entire experiment was terminated after three days. The data in FIG. 1 clearly illustrates the effectiveness of dequalinium salts against chloroquine-resistant parasites. The "Y" axis in FIG. 1 involves the percentage of erythrocytes in the test media which were infected with viable parasites. The "X" axis involves the concentration of dequalinium chloride used (in nanograms/ml.) At 0 nanograms/ml, parasite growth was extensive, with a % parasite infection of about 17 % after 72 hours. However, at a concentration level of 1.0 nanogram/ml and above, parasite growth was strongly inhibited, and after 72 hours, no viable parasites remained. Similar results were obtained with the chloroquine-sensitive strains of parasite.

The foregoing tests clearly demonstrate the remarkable effectiveness of dequalinium compounds against malaria parasites, including those which are chloroquine resistant/sensitive. Thus, the present invention represents a substantial advance in the art of malaria treatment which is urgently needed throughout the world.

Having herein described a preferred embodiment of the invention, it is anticipated that suitable modifications may be made thereto by those skilled in the art within the scope of the invention. Thus, the invention shall only be construed in accordance with the following claims:

I claim

1. A method for the treatment of malaria in warm blooded animals afflicted with malaria comprising administering a composition comprising a dequalinium salt wherein said dequalinuim salt is selected from the group consisting of an acetate, chloride bromide, iodide, and salicylate salt;
   to a warm blooded animal afflicted with malaria at a therapeutically effective level sufficient to kill malaria parasites within said animal; and
   allowing said composition to kill said malaria parasites in said animal.

2. The method of claim 1 wherein about 7.0 mg of said dequalinium salt per kg of animal body weight is administered to said animal.

3. The method of claim 1 wherein said composition is administered to said animal using a technique selected from the group consisting of subcutaneous administration, intravenous administration, intraperitoneal administration, and oral administration.

4. The method of claim 1 wherein said warm blooded animal is a human subject.

5. A method for the treatment of malaria in a human subject afflicted with malaria comprising:
   administering about 7.0 mg of a dequalinuim salt per kg of body weight to said human subject, and dequolinium salt being selected from the group consisting of an acetate, chloride, bromide, iodide and saliylatate salt, said dequalinium salt. being administered in an aqueous solution using a technique selected from the group consisting of subcutaneous administration, intravenous administration, intraperitoneal administration, and oral administration; and
   allowing said composition to kill said malaria parasites in said human subject.

* * * * *

UNITED STATES PATENT AND TRADEMARK OFFICE
CERTIFICATE OF CORRECTION

PATENT NO. : 4,946,849

DATED : Aug. 7, 1990

INVENTOR(S) : Michael T. Makler

It is certified that error appears in the above-identified patent and that said Letters Patent is hereby corrected as shown below:

In col. 2, on line 33, delete "currentlyused" and insert therefor --currently-used--.

In col. 3, on lines 32-33, delete "Tropical" and insert therefor --Topical--.

In col. 4, on line 39, delete "35:574 582" and insert therefor --135:574-582--.

In col. 5, on line 7, delete "antineoplastic" and insert therefor --anti-neoplastic--.

In col. 5, on line 21, delete "93:673-675" and insert therefor --193:673-675--.

Signed and Sealed this

Twenty-fifth Day of June, 1991

*Attest:*

HARRY F. MANBECK, JR.

*Attesting Officer*     *Commissioner of Patents and Trademarks*

UNITED STATES PATENT AND TRADEMARK OFFICE
CERTIFICATE OF CORRECTION

PATENT NO. : 4,946,849

DATED : Aug. 7, 1990

INVENTOR(S) : Michael T. Makler

It is certified that error appears in the above-identified patent and that said Letters Patent is hereby corrected as shown below:

Column 6, lines 15-25, delete claim 1 and insert therefor the following:

-- 1. A method for the treatment of malaria in warm blooded animals afflicted with malaria comprising:
    administering a composition comprising a dequalinium salt wherein said dequalinium salt is selected from the group consisting of an acetate, chloride, bromide, iodide, and salicylate salt to a warm blooded animal afflicted with malaria at a therapeutically effective level sufficient to kill malaria parasites within said animal; and
    allowing said composition to kill said malaria parasites in said animal.--

UNITED STATES PATENT AND TRADEMARK OFFICE
CERTIFICATE OF CORRECTION

PATENT NO. : 4,946,849

DATED : Aug. 7, 1990

INVENTOR(S) : Michael T. Makler

It is certified that error appears in the above-identified patent and that said Letters Patent is hereby corrected as shown below:

Column 6, lines 36-49, delete claim 5 and insert therefor the following:

-- 5. A method for the treatment of malaria in a human subject afflicted with malaria comprising:

administering about 7.0 mg of a dequalinium salt per kg of body weight to said human subject, said dequalinium salt being selected from the group consisting of an acetate, chloride, bromide, iodide, and salicylate salt, said dequalinium salt being administered in an aqueous solution using a technique selected from the group consisting of subcutaneous administration, intravenous administration, intraperitoneal administration, and oral administration; and allowing said dequalinium salt to kill said malaria parasites in said human subject. --

Signed and Sealed this

Sixth Day of October, 1992

Attest:

DOUGLAS B. COMER

Attesting Officer

Acting Commissioner of Patents and Trademarks